(12) United States Patent
Reiter

(10) Patent No.: US 8,958,072 B2
(45) Date of Patent: Feb. 17, 2015

(54) MICROPHOTOMETER

(71) Applicant: Buerkert Werke GmbH, Ingelfingen (DE)

(72) Inventor: Cyril Reiter, Ingelfingen (DE)

(73) Assignee: Buerkert Werke GmbH, Ingelfingen (DE)

( * ) Notice: Subject to any disclaimer, the term of this patent is extended or adjusted under 35 U.S.C. 154(b) by 0 days.

(21) Appl. No.: 13/943,887

(22) Filed: Jul. 17, 2013

(65) Prior Publication Data

US 2014/0034854 A1    Feb. 6, 2014

(30) Foreign Application Priority Data

Jul. 31, 2012   (DE) .................... 20 2012 007 365 U

(51) Int. Cl.
| | |
|---|---|
| *G01N 21/00* | (2006.01) |
| *G01N 21/59* | (2006.01) |
| *G01N 21/03* | (2006.01) |
| *G01N 21/05* | (2006.01) |

(52) U.S. Cl.
CPC ............ *G01N 21/59* (2013.01); *G01N 21/0303* (2013.01); *G01N 21/05* (2013.01)
USPC ......................................... 356/432; 356/436

(58) Field of Classification Search
CPC .... G02B 21/16; G02B 6/0003; G02B 27/141; G02B 6/0001; G02B 23/2469; G02B 6/0006; G02B 1/043; G02B 27/0994; G02B 27/1006; G02B 27/143; G02B 27/145; G02B 27/48; G02B 6/0008; G02B 6/0035
See application file for complete search history.

(56) References Cited

U.S. PATENT DOCUMENTS

| | | | | | |
|---|---|---|---|---|---|
| 3,740,158 | A | * | 6/1973 | Bellinger et al. | ............. 356/246 |
| 3,954,341 | A | * | 5/1976 | Uffenheimer | ................. 356/410 |
| 4,037,974 | A | * | 7/1977 | Fletcher et al. | ............... 356/246 |
| 5,125,742 | A | * | 6/1992 | Wilks, Jr. | ....................... 356/246 |
| 5,140,169 | A | * | 8/1992 | Evens et al. | .................... 250/576 |
| 6,199,257 | B1 | * | 3/2001 | Munk et al. | ...................... 29/423 |
| 6,241,948 | B1 | * | 6/2001 | Watkins et al. | ............. 422/82.05 |
| 6,385,380 | B1 | | 5/2002 | Friedrich et al. | |
| 6,542,231 | B1 | * | 4/2003 | Garrett | ......................... 356/246 |
| 7,671,974 | B2 | * | 3/2010 | O'Mahony et al. | .............. 356/39 |
| 2004/0036028 | A1 | | 2/2004 | Tao et al. | |
| 2010/0225920 | A1 | * | 9/2010 | Xia et al. | ....................... 356/442 |
| 2011/0141465 | A1 | * | 6/2011 | Jeannotte et al. | ............. 356/246 |

FOREIGN PATENT DOCUMENTS

| | | |
|---|---|---|
| DE | 10302207 A1 | 7/2004 |
| EP | 0909946 A2 | 4/1999 |
| WO | 9957584 A1 | 11/1999 |
| WO | 2012055432 A1 | 5/2012 |

OTHER PUBLICATIONS

German search report from German counterpart Application No. 20 2012 007 365.6, received on Oct. 24, 2012.

\* cited by examiner

*Primary Examiner* — Michael P Stafira
(74) *Attorney, Agent, or Firm* — Carlson, Gaskey & Olds, PC

(57) ABSTRACT

A photometer has a light source, a sensor, a liquid-core light guide which defines an optical path between the light source and the sensor and through which a liquid to be analyzed can be guided, and at least one port for the liquid. The port for the liquid to be analyzed runs through the light source.

24 Claims, 3 Drawing Sheets

MICROPHOTOMETER

RELATED APPLICATION

This application claims priority to DE 20 2012 007 365.6, which was filed 31 Jul. 2012.

TECHNICAL FIELD

The present invention relates to a photometer including a light source, a sensor, a liquid-core light guide which defines an optical path between the light source and the sensor and through which a liquid to be analyzed can be guided, and at least one port for the liquid.

BACKGROUND

Photometers of this type are known from the prior art and are used for analyzing a liquid. With the aid of a photometer, the concentration of substances in the liquid to be analyzed can be determined because the amount of the substance contained in the liquid has an effect on the absorption of light in the liquid.

Typically, the liquid to be analyzed is introduced into a vessel which is transparent to light and is irradiated by a light source from outside. The light emitted by the light source enters the liquid through a first, optically transparent, wall of the vessel and traverses the liquid to be analyzed. After the light emitted has traversed the liquid to be analyzed, the light exits from the vessel on the opposite side thereof, passing through a second, optically transparent, wall of the vessel where the light is detected by a detector that detects part of the intensity emitted. Based on the weakening of the light intensity, an indication can be obtained photometrically of the concentration of absorbing substances in the liquid.

It is also known to give the vessel a thin and elongated configuration so that a light guide is formed which is filled with the liquid to be analyzed. In order to avoid intensity losses in the course of the beam path through the liquid to be analyzed, the light is typically irradiated at a suitable angle so that the irradiated light impinges on the wall of the light guide at an angle of total reflection and is totally reflected. This requires the inner wall of the light guide to have an index of refraction that is smaller than that of the liquid to be analyzed. The angle that is appropriate for total reflection here is dependent on the indices of refraction of the wall of the light guide and of the liquid to be analyzed.

In the solutions known from the prior art, it has been found to be a disadvantage that the irradiation of light through the optically transparent vessel wall reduces the light intensity. This makes it impossible to use light sources having a low light intensity or to detect very small concentrations of the absorbing substances since because of the weakening upon entry through the first axial vessel wall, the light intensity is not sufficient for this.

Thus, there is a desire to provide a photometer which operates with lower losses and allows a precise analysis.

SUMMARY

A photometer includes a light source, a sensor, a liquid-core light guide which defines an optical path between the light source and the sensor and through which a liquid to be analyzed can be guided, and at least one port for the liquid, the port for the liquid to be analyzed running through the light source. The invention is based on the fundamental idea of minimizing or completely eliminating the intensity losses that occur during the passage through the optically transparent vessel wall. This is achieved in that the light source is arranged directly in the region which receives the liquid to be analyzed. In this way, no optically transparent partition wall leading to light intensity losses is used between the light source and the liquid to be analyzed.

In a particularly preferred embodiment, the sensor includes a port for the liquid to be analyzed, the port running through the sensor. This provides low-loss conditions on the sensor side as well, since the number of light transitions is minimized, with the liquid to be analyzed running directly through the sensor.

More particularly, the liquid-core light guide includes a cladding which is mechanically connected with the light source. The cladding defines the path of the liquid through the liquid-core light guide. In addition, the cladding is preferably made from a material which allows the light irradiated into the liquid-core light guide to be totally reflected. To this end, the cladding has an index of refraction which is lower than that of the liquid in the liquid-core light guide.

Preferably, the cladding is received in a seat of the light source. This offers the advantage that there is a low-loss connection between the light source and the liquid-core light guide since the light radiated by the light source is emitted directly into the liquid-core light guide without an occurrence of light intensity losses.

In one particular embodiment, the light source is an LED having a plastic body which is provided with a port opening for the liquid to be analyzed. Having the light source in the form of an LED is particularly advantageous because this provides an especially compact light source. Further, an LED has a defined wavelength and, in addition, it is particularly efficient. The configuration with a plastic body is to be preferred in that this produces a liquid-resistive light source which can receive part of the liquid-core light guide.

Preferably, the LED includes a positioning surface. This simplifies assembly because the flattened positioning surface allows a precise orientation of the LED in the photometer.

In particular, the port opening opens in the positioning surface. This surface is especially suitable for the port opening because the surface is a flat surface, which allows the LED and the port opening to be sealed at this surface in a simple manner, for example by a sealing ring.

The port opening advantageously opens in the seat. This reduces the intensity losses further and provides a protection from parasitic scattered light because the cladded liquid-core light guide is received in the seat and, therefore, the liquid to be analyzed is introduced directly via the light source into the liquid-core light guide, as a result of which no intensity losses occur and, in addition, no other light sources can have an impact.

The sensor is preferably a photosensor. Because the sensor detects the light emitted by the light source, it is of advantage that the sensor is a photosensor which responds to the emitted light.

In a preferred embodiment, the photometer has a modular structure. This offers the advantage that individual components of the photometer can be exchanged in case they are defective or need to be refitted for other purposes.

More specifically, the photometer includes a light source block and a sensor block. The two-component structure of the photometer with a light source block and a sensor block ensures that different light sources can be used, for example. It is also possible to exchange the sensor block with the sensor arranged thereon, where this is required by a particular application.

In one embodiment, the light source block and/or the sensor block is/are made of metal. As a result, the two modules are in the form of very solid components, which has the advantage that they are very sturdy and resistant to media, which may be of advantage depending on the application site.

According to a further embodiment, the light source block and/or the sensor block may be made of plastic. The production of the modules from plastic has the advantage that they can be produced at very low cost, for example in an injection molding process.

In particular, the light source block and the sensor block each include a port for the liquid to be analyzed. This ensures that the liquid to be analyzed can be analyzed over a liquid path that is as long as possible since the two ports are arranged close to the sensor and close to the light source, respectively.

More particularly, the light source is releasably attached to the light source block. Thus, a faulty or malfunctioning light source can be replaced simply and quickly without detaching the light source block from the rest of the photometer. In addition, it is possible to exchange the light source for a particular area of application, so that the photometer can be made use of for a variety of fields of application.

The light source block preferably includes a holding bore for the liquid-core light guide. In this way, the liquid-core light guide can be supported within the light source block. Due to the intended total reflection in the liquid-core light guide, the position of the liquid-core light guide in relation to the light source is particularly relevant and critical. The position of the liquid-core light guide in relation to the light source is defined by the holding bore.

In particular, the sensor is releasably attached to the sensor block. This ensures that the sensor can be exchanged, which may be required, for example, if the sensor is defective, or else if a different sensor is better suited for a different area of application than the previous one. This generally increases the flexibility of the photometer since the photometer can be adapted to a variety of fields of application by an exchange of the sensor.

Preferably, the sensor is fitted within a separate holder which is mounted to the sensor block. The separate mounting of the sensor allows the sensor to be exchanged even more simply since during such exchange, the complete sensor block may remain connected with the light source block, and only the separate holder of the sensor needs to be exchanged or released.

The holder may be fitted to the sensor block with a sealing film which is preferably transparent and self-adhesive. The single film thereby provides the required sealing function of the liquid-core light guide and the holding function for fastening the holder to the sensor block, which saves material.

The photometer according to the invention typically has a length of 30 mm, the length being dependent on the length of the liquid-core light guide, so that lengths of 20 mm to 100 mm are also possible. The photometer further has a width of about 15 mm and a height of 15 mm. It is apparent from this that the photometer according to the invention is a microphotometer, since its dimensions are very compact.

In a particularly preferred embodiment, the light source and/or the sensor was/were at least partly produced in an injection molding process. This offers the advantage that they can be produced at low cost and the ports can already be produced during the production of the light source and/or of the sensor.

BRIEF DESCRIPTION OF THE DRAWINGS

Further features and advantages of the invention will be apparent from the description below and from the accompanying drawings, to which reference is made and in which.

DETAILED DESCRIPTION

Figure 1:
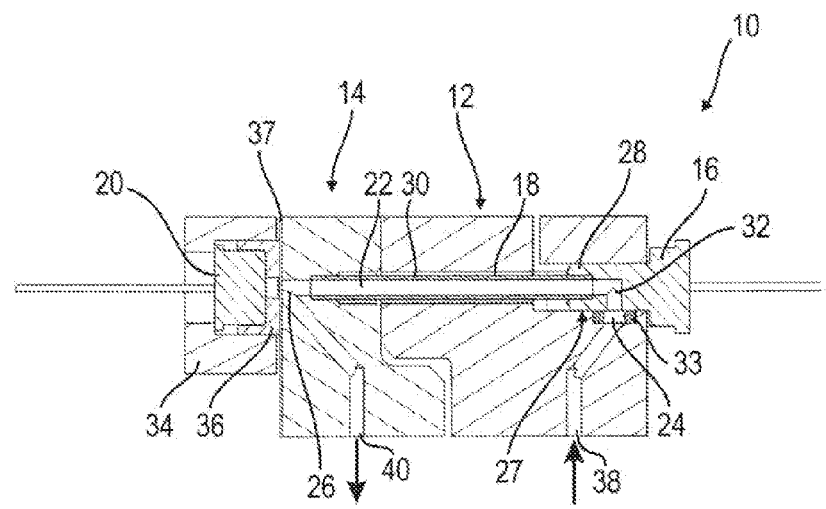
FIG. 1 shows a sectional view of a photometer according to the invention, in an assembled condition.

FIG. 1 shows a photometer 10 which includes a light source block 12 and a sensor block 14. The light source block 12 includes a light source 16 and a liquid-core light guide 18. In the assembled condition, the liquid-core light guide 18 extends from the light source block 12 as far as into the sensor block 14. Furthermore, the sensor block 14 includes a sensor 20 which is in the form of a photodiode.

A liquid 22 to be analyzed is guided through the liquid-core light guide 18; the liquid 22 to be analyzed enters the liquid-core light guide 18 via a port 24 in the light source block 12 and, after passing through the liquid-core light guide 18, exits the liquid-core light guide 18 via a port 26 on the sensor block 14.

The light source 16 is configured as a light-emitting diode (LED), for example, and includes a positioning surface 27 by which the light source 16 can be precisely positioned within the light source block 12. In addition, the light source 16 includes a seat 28 for the liquid-core light guide 18. The liquid-core light guide 18 has a cladding 30 which is mechanically connected with the seat 28. Traversing its seat 28, the light source 16 further includes a port opening 32 for the port 24, whereby the flow path of the liquid 22 to be analyzed partly runs through the light source 16, with the port opening 32 being provided at the positioning surface 27 of the light source 16.

Figure 2:
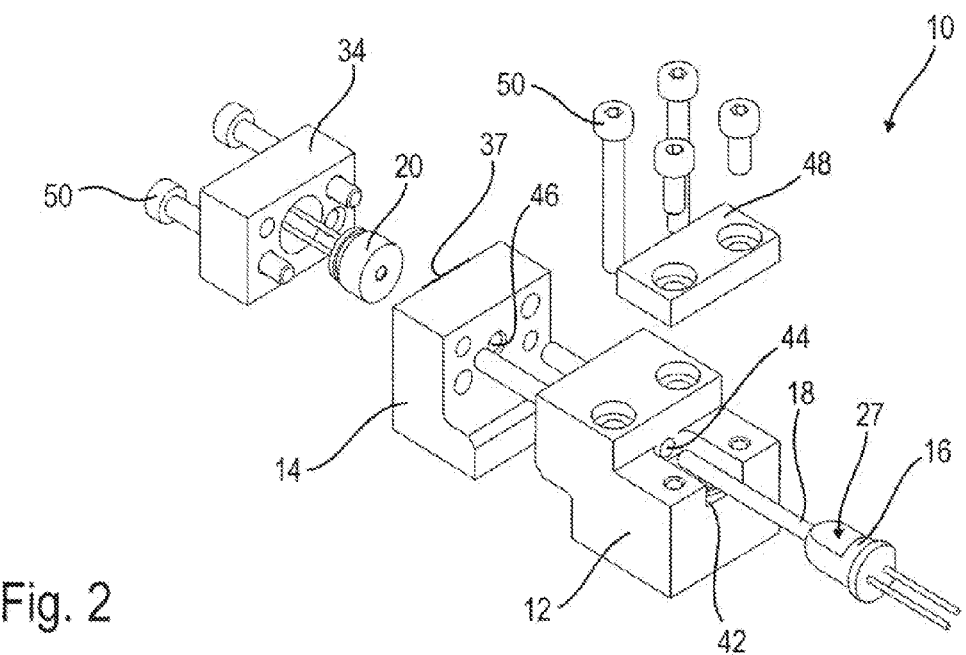
FIG. 2 shows an exploded view of the photometer according to the invention as shown in FIG. 1.

Together with the cladding 30, the LED 16 constitutes an integrated assembly which can be exchanged in a simple manner (see in particular FIG. 2).

In the sensor block 14, the sensor 20 is arranged at a holder 34 which is releasably connected with the main element of the sensor block 14. The sensor block 14 further includes a diaphragm 36 which is also arranged at the holder 34 and positioned in front of the sensor 20. A film 37 is arranged between the holder 34 and the sensor block 14. The film 37 is made to be transparent, in particular self-adhesive. In this way, the sensor block 14 is sealed.

Here, the operating principle of the photometer 10 is as follows:

The photometer 10 according to the invention analyzes the liquid 22 to be analyzed and which has been introduced into the liquid-core light guide 18 in that light emitted by the light source 16 passes through the liquid-core light guide 18 with the liquid 22 to be analyzed contained therein and impinges on the sensor 20. The light path through the liquid-core light guide 18 will be explained in detail with reference to FIG. 5.

The liquid 22 to be analyzed is introduced into the light source block 12 via an inlet 38. The liquid 22 to be analyzed moves into the light source 16 via the port 24 and the port opening 32 of the light source 16. The transition between the inlet 38 and the port opening 32 is sealed with a sealing ring 33. Further arranged in the seat 28 of the light source 16 is the liquid-core light guide 18. Because the port opening 32 through which the liquid 22 to be analyzed is introduced into the light source 16 is also arranged in the seat 28 of the light source 16, the liquid 22 to be analyzed moves directly into the liquid-core light guide 18. The liquid 22 to be analyzed thus flows directly through the light source 16 because the port 24 for the liquid 22 to be analyzed leads directly into the light source 16. The liquid 22 to be analyzed then flows from the light source block 12 into the sensor block 14 via the liquid-core light guide 18 surrounded by the cladding 30. From the sensor block 14, the liquid 22 to be analyzed can flow through the port 26 and finally leaves the sensor block 14 at the outlet 40.

Generally, it is also possible to interchange the inlet 38 and the outlet 40, so that the liquid 22 to be analyzed is introduced into the sensor block 14 and exits from the light source block 12.

While the liquid 22 to be analyzed is present in the liquid-core light guide 18, the light source 16 emits a light signal which likewise passes through the liquid-core light guide 18 and is detected by the sensor 20 in the sensor block 14. The principle of the light wave path in the liquid-core light guide 18 will be explained with reference to FIG. 5.

Because the liquid 22 to be analyzed passes directly through the light source 16, in the configuration as shown of the photometer 10, the losses with regard to the light intensity are particularly low. In addition, the cladding 30 of the liquid-core light guide 18 and the connection of the liquid-core light guide 18 with the light source 16 within the seat 28 ensure that the liquid 22 to be analyzed, which is present in the liquid-core light guide 18, is protected from any parasitic light sources that impair the analysis or the light emitted by the light source 16.

As an alternative to the embodiment shown here, the sensor 20 may also be arranged directly on the sensor block 14 and be sealed by a sealing ring, for example, by analogy with the light source 16 and the light source block 12.

In another particularly preferred embodiment, the port 26 on the sensor block 14 is integrated directly in the sensor 20, as a result of which, by analogy with the light source 16, the liquid-core light guide 18 extends through the sensor 20, thus minimizing the number of light transitions. In this embodiment, it presents itself to produce the light source 16 and the sensor 20 from a plastic material and, in doing so, already produce the ports 24, 26 in an injection molding process.

FIG. 2 shows an exploded view of the photometer 10, clearly illustrating the modular structure of the photometer 10. Accordingly, the photometer 10 can be subdivided into several blocks or functional elements. The light source block 12 is shown, which includes a contact surface 42 for the positioning surface 27 of the light source 16. This contact surface 42 and the positioning surface 27 of the light source 16 allow the light source 16 to be positioned and aligned. The light source block 12 further includes a holding bore 44 for the liquid-core light guide 18. The liquid-core light guide 18 is supported in this holding bore 44 and is therefore precisely aligned with the light source 16.

A further module shown is the sensor block 14, which is shaped to allow it to be connected with the light source block 12 in a substantially form-fitting manner. The sensor block 14 further includes a duct 46 which is also provided to receive the liquid-core light guide 18. The holder 34 is part of the sensor block 14; in the figure shown, the holder 34 is illustrated at a distance from this sensor block 14 since it is generally releasably connected with the main part of the sensor block 14. Arranged at the holder 34 is the sensor 20 which, together with the light source 16 and the liquid-core light guide 18, forms the heart of the photometer 10. The sealing film 37 is arranged between the holder 34 and the sensor block 14.

Further shown in FIG. 2 is a securing member 48 which, together with the light source block 12, secures the light source 16. Owing to the securing member 48, the light source 16, when in the installed condition, can be exchanged quickly and simply since this only requires the securing member 48 to be removed, for the light source 16 to be freely accessible. This obviates the need to completely disassemble the photometer 10 to exchange the light source 16 and the cladding 30 of the liquid-core light guide.

Further shown are fixing members 50 for fixing the individual modules of the photometer 10 to each other.

Figure 3:
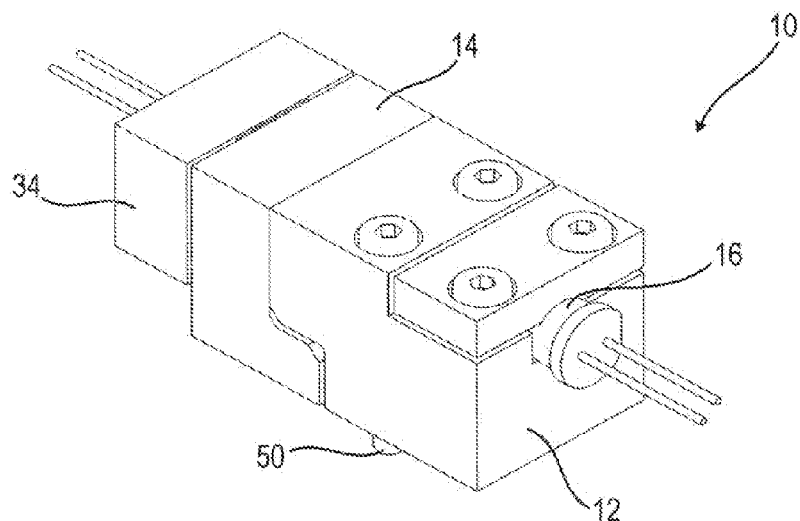
FIG. 3 shows a perspective view of the photometer according to the invention as shown in FIGS. 1 and 2, in the assembled condition.

FIG. 3 shows the photometer 10 from FIG. 2 in the installed condition. Only the various modules of the modularly structured photometer 10 are visible from outside. In the light source block 12, the end of the light source 16 and one of a plurality of protruding screws 50 can be seen from outside here; the screws 50 can be used for fastening the photometer 10 onto a base plate, for example. Further visible on the light source block 12 are the securing member 48 which serves to secure the light source 16, and the fixing members 50 in the installed condition. The sensor block 14 with the holder 34 arranged thereon is also visible from outside in FIG. 3.

Figure 4:
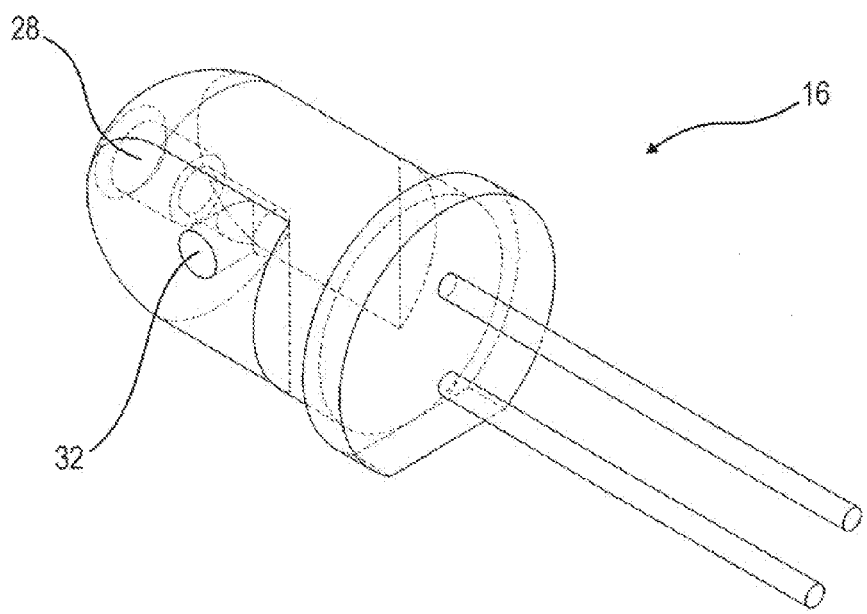
FIG. 4 shows a perspective view of a light source from the preceding figures.

FIG. 4 shows the light source 16 in detail. The port opening 32, through which the liquid 22 to be analyzed is introduced into the light source 16, is clearly visible here. Also visible is the seat 28 which receives the liquid-core light guide 18 along with the cladding 30 and in this way establishes the fluid communication with the port opening 32 through the light source 16. In addition to the light-emitting function, the light source 16 therefore serves as a connecting element of the liquid port 24 and the liquid-core light guide 18, so that the liquid 22 to be analyzed can be guided from the inlet 38 via the light source 16 directly into the liquid-core light guide 18.

Figure 5:
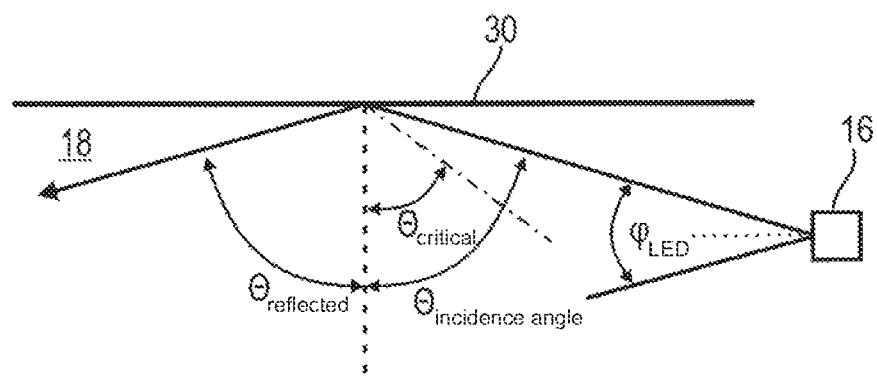
FIG. 5 shows a diagram for illustrating the light path of the light emitted by the light source through the liquid-core light guide.

FIG. 5 shows a diagram that illustrates the optical path within the liquid-core light guide 18. The light emitted by the light source 16 is incident on the surface of the cladding 30 at a specific angle $\theta_{incidence\ angle}$, the cladding 30 surrounding the liquid-core light guide 18. When selecting the material of the cladding 30, it should be made sure that the material has a lower index of refraction than the liquid 22 to be analyzed which flows through the liquid-core light guide 18. This ensures that as of a specific critical angle $\theta_{critical}$, the entire light emitted by the light source 16 is reflected. This critical angle $\theta_{critical}$ for total reflection here depends on the index of refraction of the liquid 22 $n_{liquid}$ to be analyzed and on the index of refraction of the cladding 30 $n_{cladding}$.

Total reflection therefore occurs if the following condition for the incidence angle $\theta_{incidence\ angle}$ is met:

$$\theta_{incidence\ angle} = 90° - \frac{\varphi_{LED}}{2} > \theta_{critical},$$

with the illumination angle of the LED $\varphi_{LED}$, where the following is applicable to the critical angle $\theta_{critical}$:

$$\theta_{critical} = \sin^{-1}\frac{n_{cladding}}{n_{liquid}} * \frac{180°}{\pi},$$

with the indices of refraction of the cladding 30 $n_{cladding}$ and of the liquid 22 $n_{liquid}$ to be analyzed. According to the invention, a modularly structured photometer 10 is provided in this way which operates with lower losses and is therefore suitable for the use of light sources 16 which have only a very low intensity, and for detecting minimum concentrations of absorbing substances in the liquid 22 to be analyzed.

Although an embodiment of this invention has been disclosed, a worker of ordinary skill in this art would recognize that certain modifications would come within the scope of this disclosure. For that reason, the following claims should be studied to determine the true scope and content of this disclosure.

The invention claimed is:

1. A photometer comprising:
a light source having an emitting surface comprising at least one port opening through which liquid to be analyzed can flow;
a sensor; and
a liquid-core light guide which defines an optical path between the light source and the sensor and through which the liquid to be analyzed can be guided.

2. The photometer according to claim 1, wherein the sensor includes a port for the liquid to be analyzed, the port running through the sensor.

3. The photometer according to claim 2, wherein the liquid-core light guide includes a cladding which is mechanically connected with the light source.

4. The photometer according to claim 3, wherein the cladding is received in a seat of the light source.

5. The photometer according to claim 4, wherein the light source is an LED having a plastic body which is provided with the port opening for the liquid to be analyzed.

6. The photometer according to claim 5, wherein the LED includes a positioning surface.

7. The photometer according to claim 6, wherein the port opening opens in the positioning surface.

8. The photometer according to claim 5, wherein the port opening opens in the seat.

9. The photometer according to claim 1, wherein the sensor is a photosensor.

10. The photometer according to claim 1, wherein the photometer has a modular structure.

11. The photometer according to claim 1, wherein the photometer includes a light source block and a sensor block.

12. The photometer according to claim 11, wherein the light source block and/or the sensor block is/are made of metal.

13. The photometer according to claim 11, wherein the light source block and/or the sensor block is/are made of plastic.

14. The photometer according to claim 11, wherein the light source block and the sensor block each include a port for the liquid to be analyzed.

15. The photometer according to claim 11, wherein the light source is releasably attached to the light source block.

16. The photometer according to claim 11, wherein the light source block includes a holding bore for the liquid-core light guide.

17. The photometer according to claim 11, wherein the sensor is releasably attached to the sensor block.

18. The photometer according to claim 17, wherein the sensor is fitted within a separate holder which is mounted to the sensor block.

19. The photometer according to claim 18, wherein the holder is fitted to the sensor block with a sealing film which is transparent and self-adhesive.

20. The photometer according to claim 1, wherein the light source and/or the sensor was/were at least partly produced in an injection molding process.

21. The photometer according to claim 1, wherein the light source comprises an origin of light emitted to analyze the liquid.

22. The photometer according to claim 21, including a light source block with a contact surface against which the light source rests.

23. The photometer according to claim 22, including a sensor block associated with the sensor, the sensor block being directly attached to the light source block.

24. The photometer according to claim 23, wherein the liquid-core light guide has a first end directly connected to the light source and extends through the light source block to a second end that terminates within the sensor block.

* * * * *